United States Patent [19]

Schroeder et al.

[11] Patent Number: 4,933,492

[45] Date of Patent: Jun. 12, 1990

[54] PURIFICATION OF CRUDE ISOPHTHALIC ACID

[75] Inventors: Hobe Schroeder, Warrenville; Ricky L. Wittman, Aurora, both of Ill.

[73] Assignee: Amoco Corporation, Chicago, Ill.

[21] Appl. No.: 419,656

[22] Filed: Oct. 11, 1989

Related U.S. Application Data

[63] Continuation of Ser. No. 257,511, Oct. 13, 1988, abandoned.

[51] Int. Cl.$^5$ ............................................. C07C 51/487
[52] U.S. Cl. ...................................... 562/487; 560/78; 562/486
[58] Field of Search ......................................... 562/487

[56] References Cited

U.S. PATENT DOCUMENTS

| 3,584,039 | 6/1971 | Meyer | 562/487 X |
| 3,726,915 | 4/1973 | Pohlmann | 562/487 |
| 4,405,809 | 9/1983 | Stech et al. | 562/487 |
| 4,467,110 | 8/1984 | Puskas et al. | 562/487 |
| 4,626,598 | 12/1986 | Packer et al. | 562/487 |

Primary Examiner—Werren B. Lone
Assistant Examiner—Vera C. Clarke
Attorney, Agent, or Firm—James R. Henes; William H. Magidson; Ralph C. Medhurst

[57] ABSTRACT

Solutions of crude isophthalic acid are purified by hydrogenation in the presence of a catalyst comprising two Group VIII noble metal-containing components.

19 Claims, No Drawings

PURIFICATION OF CRUDE ISOPHTHALIC ACID

This is a continuation of application Ser. No. 257,511, filed Oct. 13, 1988, now abandoned.

BACKGROUND OF THE INVENTION

1. Field of the Invention

This invention relates generally to a method for the catalytic purification of crude isophthalic acid and to the catalyst system employed therein, and more particularly concerns the use in such purification of a catalyst bed comprising Group VIII noble metal components comprising at least two of palladium-, platininum-, rhodium-, ruthenium-, osmium-, and iridium-containing components.

2. Discussion of the Prior Art

Polymer grade or "purified" isophthalic acid is one of the starting materials which are employed in the manufacture of unsaturated polyesters. Purified isophthalic acid is derived from relatively less pure, technical grade or "crude" isophthalic acid by purification of the latter utilizing hydrogen and a noble metal catalyst, of the type described in Meyer, U.S. Pat. No. 3,584,039 or Stech et al., U.S. Pat. No. 4,405,809 for the purification of crude terephthalic acid. In the purification process, the crude isophthalic acid is dissolved in water at an elevated temperature, and the resulting solution is hydrogenated, preferably in the presence of a hydrogenation catalyst containing a noble metal, typically palladium, on a carbon support, as described in Pohlmann, U.S. Pat. No. 3,726,915 for the purification of crude terephthalic acid. This hydrogenation step converts the various color bodies present in the crude isophthalic acid to colorless products.

However, even after the aforesaid purification, the purified isophthalic acid product contains color bodies. Therefore, it is highly desirable to reduce the concentration of such color bodies that remain in purified isophthalic acid. The color level of purified isophthalic acid product is generally measured directly either by measuring the optical density of solutions of purified isophthalic acid or the b*-value of the solid purified isophthalic acid itself. The optical density of purified isophthalic acid is measured as the absorbance of light at 340 and 400 nanometers (nm) in its basic solution in a solvent such as sodium hydroxide or ammonium hydroxide.

The measurement of the b*-value of a solid on the Hunter Color Scale is described in Hunter, *The Measurement of Appearance*, Chapter 8, pp. 102–132, John Wiley & Sons, N.Y., N.Y. (1975), and in Wyszecki et al., Color Science, *Concepts and Methods, Quantitative Data and Formulae*, 2d Ed., pp. 166–168, John Wiley & Sons, N.Y., N.Y. (1982).

More specifically, the b*-value of purified isophthalic acid can be determined using, for example, a Diano Match Scan Spectrophotometer as follows. Purified isophthalic acid is pressed into a pellet having a thickness of about 0.25 inch and a diameter of about 1 inch. The pellet is then irradiated with white light that has been UV-filtered. The spectrum of the visible light reflected from the sample is determined and tristimulus values (X, Y, and Z) are computed using the CIE Standard Observer functions. Using the weighted-ordinate method, tristimulus values are obtained from the following equations:

$$X = \sum_{400}^{700} R_\lambda \bar{x}_\lambda, \quad Y = \sum_{400}^{700} R_\lambda \bar{y}_\lambda, \quad Z = \sum_{400}^{700} R_\lambda \bar{z}_\lambda,$$

where $R_\lambda$ is the percent reflectance of the object at wavelength $\lambda$ and $\bar{x}_\lambda$, $\bar{y}_\lambda$, and $\bar{z}_\lambda$ are the Standard Observer functions at wavelength $\lambda$ for CIE Illuminant D65. The tristimulus values, X, Y and Z, identify the color of the object in terms of the mixture of the primary lights that match it visually. Tristimulus values, however, are of limited use as color specifications, because they do not correlate with visually meaningful attributes of color appearance and are not uniform in the spacing of colors as related to visual differences. As a result, "Uniform Color Scales" (UCS) have been adopted which use simple equations to approximate visual response. The UCS scale used by the Diano instrument is the CIE 1976 L*a*b* formula which converts tristimulus values to L*, a*, and b* values as shown below:

$$L^* = 25(100Y/Y_o)^{\frac{1}{3}} - 16$$

$$a^* = 500[(X/X_o)^{\frac{1}{3}} - (Y/Y_o)^{\frac{1}{3}}]$$

$$b^* = 200[(Y/Y_o)^{\frac{1}{3}} - (Z/Z_o)^{\frac{1}{3}}]$$

The L*-value is a measure of the luminosity or whiteness of an object where L*=100 is pure white, L*=0 is black, and in between is gray. The L*-value is strictly a function of the tristimulus Y-value. The b*-value is a measure of the yellowness-blueness attribute where positive b*-values represent yellow appearance and negative b*-values represent blue appearance. The b*-value is a function of both tristimulus values Y and Z.

Furthermore, even after purification, the purified isophthalic acid product often contains impurities which fluoresce at wavelengths of about 390 and 400 nanometers (nm) upon excitation at wavelengths of 260–320 nanometers. Further reduction of such fluorescence of the purified isophthalic acid product is highly desirable. Since the concentration of such impurities in purified isophthalic acid can vary significantly, specifications are often established for the amount of such fluorescence which can be permitted for the purified isophthalic acid product. The problem of the control of such fluorescence by purified isophthalic acid is complicated because some of the fluorescent impurities are soluble and can be removed by conventional procedures for purifying isophthalic acid while other such fluorescent impurities are insoluble and cannot be removed by such conventional procedures. Furthermore, upon chemical reduction during purification of crude isophthalic acid, some impurities which do not themselves fluoresce at wavelengths of 390 and 400 nanometers upon excitation at wavelengths of 260–320 nanometers are converted to their reduced forms which fluoresce at 390 and 400 nanometers upon excitation by wavelengths of 260–320 nanometers.

Puskas et al., U.S. Pat. Nos. 4,394,299 and 4,467,110 disclose the use of a combination noble metal catalyst, for example, a palladium/rhodium catalyst on a porous carbonaceous surface, for purification of aqueous terephthalic acid solutions. These two patents also show the use of a rhodium-on-carbon catalyst under reducing conditions and review various heretofore known methods of preparing a Group VIII metal catalyst having activity and selectivity suitable for the purification of terephthalic acid by hydrogenating its principal impurity, 4-carboxybenzaldehyde, to p-toluic acid.

We have now discovered that the use in the aforesaid purification of crude isophthalic acid of a catalyst system comprising metal components comprising at least two of palladium-, platinum-, rhodium-, ruthenium-, osmium- and iridium-containing components supported on active carbon carrier particles, and the passage of the aqueous solution of crude isophthalic acid through a bed of the aforesaid catalyst particles effects a further decrease in the concentration of color bodies and of fluorescent impurities in the resulting purified isophthalic acid, relative to the use of a conventional palladium-on-carbon catalyst alone.

SUMMARY OF THE INVENTION

The present invention is a method for the purification of crude isophthalic acid comprising: passing an aqueous solution of said crude isophthalic acid, at a temperature of from about 100° C. to about 300° C. and at a pressure that is sufficient to maintain the solution substantially in the liquid phase, through a particulate catalyst bed and in the presence of hydrogen; said particulate catalyst bed comprising Group VIII noble metal-containing components comprising at least two of palladium-, platinum-, rhodium-, ruthenium-, osmium- and iridium-containing components, supported on active carbon carrier particles; and thereafter cooling the resulting hydrogenated aqueous solution to effect separation of the resulting purified isophthalic acid from said solution by crystallization.

DETAILED DESCRIPTION INCLUDING PREFERRED EMBODIMENTS

The method of this invention is particularly suitable for use in the purification of crude isophthalic acid prepared by the continuous catalytic, liquid-phase oxidation of m-xylene in a solvent. Suitable solvents for use in the catalytic, liquid-phase oxidation of m-xylene include any aliphatic $C_2$-$C_6$ monocarboxylic acid such as acetic acid, propionic acid, n-butyric acid, isobutyric acid, n-valeric acid, trimethylacetic acid, and caproic acid, and water and mixtures thereof. Preferably, the solvent is a mixture of acetic acid and water, which more preferably contains from 1 to 20 weight percent of water, as introduced into the oxidation reactor. Since heat generated in the highly exothermic liquid-phase oxidation is dissipated at least partially by vaporization of solvent in the oxidation reactor, some of the solvent is withdrawn from the reactor as a vapor, which is then condensed and recycled to the reactor. In addition, some solvent is withdrawn from the reactor as a liquid in the product stream. After separation of the crude isophthalic acid product from the product stream, at least a portion of the mother liquor (solvent) in the resulting product stream is generally recycled to the reactor.

The source of molecular oxygen employed in the oxidation step of the method for producing purified isophthalic acid can vary in molecular oxygen content from that of air to oxygen gas. Air is the preferred source of molecular oxygen. In order to avoid the formation of explosive mixtures, the oxygen-containing gas fed to the reactor should provide an exhaust gas-vapor mixture containing from 0.5 to 8 volume percent oxygen (measured on a solvent-free basis). For example, a feed rate of the oxygen-containing gas sufficient to provide oxygen in the amount of from 1.5 to 2.8 moles per methyl group will provide such 0.5 to 8 volume percent of oxygen (measured on a solvent-free basis) in the gas-vapor mixture in the condenser.

The catalyst employed in the oxidation step of the method for producing crude isophthalic acid comprises cobalt, manganese, and bromine components, and can additionally comprise accelerators known in the art. The weight ratio of cobalt (calculated as elemental cobalt) in the cobalt component of the catalyst-to-m-xylene in the liquid-phase oxidation is in the range of from about 0.2 to about 10 milligram atoms (mga) per gram mole of m-xylene. The weight ratio of manganese (calculated as elemental manganese) in the manganese component of the catalyst-to-cobalt (calculated as elemental cobalt) in the cobalt component of the catalyst in the liquid-phase oxidation is in the range of from about 0.2 to about 10 mga per mga of cobalt. The weight ratio of bromine (calculated as elemental bromine) in the bromine component of the catalyst-to-total cobalt and manganese (calculated as elemental cobalt and elemental manganese) in the cobalt and manganese components of the catalyst in the liquid-phase oxidation is in the range of from about 0.2 to about 1.5 mga per mga of total cobalt and manganese.

Each of the cobalt and manganese components can be provided in any of its known ionic or combined forms that provide soluble forms of cobalt, manganese, and bromine in the solvent in the reactor. For example, when the solvent is an acetic acid medium, cobalt and/or manganese carbonate, acetate tetrahydrate, and/or bromine can be employed. The 0.2:1.0 to 1.5:1.0 bromine-to-total cobalt and manganese milligram atom ratio is provided by a suitable source of bromine. Such bromine sources include elemental bromine ($Br_2$), or ionic bromide (for example, HBr, NaBr, KBr, $NH_4Br$, etc.), or organic bromides which are known to provide bromide ions at the operating temperature of the oxidation (e.g., bromobenzenes, benzylbromide, mono- and di-bromoacetic acid, bromoacetyl bromide, tetrabromoethane, ethylene-di-bromide, etc.). The total bromine in molecular bromine and ionic bromide is used to determine satisfaction of the elemental bromine-to-total cobalt and manganese milligram atom ratio of 0.2:1.0 to 1.5:1.0. The bromine ion released from the organic bromides at the oxidation operating conditions can be readily determined by known analytical means. Tetrabromoethane, for example, at operating temperatures of 170° C. to 225° C. has been found to yield about 3 effective gram atoms of bromine per gram mole.

In operation, the minimum pressure at which the oxidation reactor is maintained is that pressure which will maintain a substantial liquid phase of the m-xylene and at least 70 percent of the solvent. The m-xylene and solvent not in the liquid phase because of vaporization are removed from the oxidation reactor as a vapor-gas mixture, condensed, and then returned to the oxidation reactor. When the solvent is an acetic acid-water mixture, suitable reaction gauge pressures in the oxidation reactor are in the range of from about 0 kg/cm$^2$ to about 35 kg/cm$^2$, and typically are in the range of from about 10 kg/cm$^2$ to about 30 kg/cm$^2$. The temperature range within the oxidation reactor is generally from about 120° C., preferably from about 150° C., to about 240° C. The solvent residence time in the oxidation reactor is generally from about 20 to about 150 minutes and preferably from about 30 to about 120 minutes.

The resulting product is a slurry of relatively impure or crude isophthalic acid that includes relatively large amounts of impurities such as 3-carboxybenzaldehyde, which impurities can be present in amounts up to about 10,000 parts per million parts of isophthalic acid, by weight. These impurities adversely affect the isophthalic acid polymerization reactions which produce unsaturated polyesters as well as may cause undesirable coloring of the resulting unsaturated polyester polymers.

The process embodying the present invention is conducted at an elevated temperature and pressure in a fixed catalyst bed. Both down-flow and up-flow reactors can be used. The crude isophthalic acid to be purified is dissolved in water or a like polar solvent. Water is the preferred solvent; however, other suitable polar solvents are the relatively lower molecular weight alkyl carboxylic acids, alone or admixed with water. Hydrogenation of 3-carboxybenzaldehyde to m-toluic acid is one of the principal reactions that occur in the catalyst bed.

Reactor, and thus isophthalic acid solution, temperatures during purification can be in the range of about 100° C. (about 212° F.) to about 300° C. (about 572° F.). Preferably the temperatures are in the range of about 200° C. (about 392° F.) to about 250° C. (about 482° F.).

Reactor pressure conditions primarily depend upon the temperature at which the purification process is carried out. Inasmuch as the temperatures at which practical amounts of the impure isophthalic acid may be dissolved are substantially above the normal boiling point of the polar solvent, the process pressures are necessarily considerably above atmospheric pressure to maintain the isophthalic acid solution in liquid phase. If the reactor has a head space, the reactor pressure can be maintained by gaseous hydrogen alone or in admixture with an inert gas such as water vapor and/or nitrogen in the head space. The use of an inert gas in admixture with hydrogen also can provide an advantageous means for modulating the reactor hydrogen partial pressure, especially at relatively low hydrogen partial pressures. To this end, the inert gas preferably is admixed with hydrogen prior to introduction into the reactor. In general, the reactor pressure during hydrogenation can be in the range of about 100 to about 1000 pounds per square inch gauge (psig), and usually is in the range of about 350 psig to about 450 psig.

The hydrogenation reactor can be operated in several modes. For example, a predetermined liquid level can be maintained in the reactor and hydrogen can be fed in, for any given reactor pressure, at a rate sufficient to maintain the predetermined liquid level. The difference between the actual reactor pressure and the vapor pressure of the isophthalic acid solution present is the hydrogen partial pressure in the reactor vapor space. Alternatively, if hydrogen is fed in admixture with an inert gas such as nitrogen, the difference between the actual reactor pressure and the vapor pressure of the isophthalic acid solution present is the combined partial pressure of hydrogen and the inert gas admixed therewith. In this case the hydrogen partial pressure can be calculated from the known relative amounts of hydrogen and inert gas present in the admixture.

In the operating mode where process control is effected by adjusting the hydrogen partial pressure, the hydrogen partial pressure in the reactor preferably is in the range of about 10 psi to about 200 psi, or higher, depending upon the service pressure rating of the reactor, the degree of contamination of the impure isophthalic acid, the activity and age of the particular catalyst employed, and like processing considerations.

A suitable palladium-on-carbon catalyst can be obtained, for example, from Engelhard Corporation, Newark, N.J., under the designation "Palladium on Activated Carbon Granules (Carbon Code CG-5)." Similarly, suitable rhodium-on-carbon catalysts can be obtained from Engelhard Corporation, under the designations "Rhodium on Activated Carbon Granules (Carbon Code CG-5)" and "Rhodium on Activated Carbon Granules (Carbon Code CG-21)." Both of these rhodium-on-carbon catalysts have a $N_2$ BET surface area of about 1,000 $m^2$/gram and have a particle size of $4 \times 8$ mesh, U.S. Sieve Series. Other suitable rhodium-on-carbon and palladium-on-carbon catalysts of similar size and surface area are available from Johnson Matthey Inc., Seabrook, N.H., under the designation "11766 Rhodium, 1% on Steam Activated Carbon Granules, Anhydrous." Similarly, suitable ruthenium-on-carbon, platinum-on-carbon and iridium-on-carbon catalysts are also commercially available.

The catalyst carrier is active carbon, usually that derived from coconut charcoal in the form of granules having a surface area of at least about 600 $m^2$/g ($N_2$; BET Method), preferably about 800 $m^2$/g to about 1,500 $m^2$/g. However, other porous carbonaceous supports or substrates can be used as long as the surface area requirements can be met. In addition to coconut charcoal, activated carbon derived from other plant or from animal sources can be utilized.

The loading of each of the palladium, ruthenium, rhodium, platinum, osmium or iridium employed on the carrier is in the range of about 0.01 weight percent to about 2 weight percent, based on the total weight of the catalyst, i.e., metal plus active carbon carrier, and calculated as elemental metal. Preferably the loading of each catalyst metal employed is about 0.5 weight percent.

In one embodiment of the method of the present invention, the Group VIII noble metal-containing components are supported on the same active carbon carrier particles and thus there is a substantially uniform distribution of each of the Group VIII noble metal-containing components throughout the catalyst bed. In this embodiment, a particular active carbon carrier particle contains all of the Group VIII noble metal-containing components, and the relative amounts of the Group VIII noble metals in the catalyst bed are controlled by the relative amounts of the two Group VIII noble metals on each catalyst particle.

In the alternative, and preferably, one of the Group VIII noble metal-containing components is supported on a first group of the active carbon carrier particles, and a second Group VIII noble metal-containing component is supported on a second group of the active carbon carrier particles, and the aforesaid first group of particles is separate and distinct from the aforesaid second group of particles. In this embodiment, a particular active carbon carrier particle contains only one Group VIII noble metal-containing component; and the relative amounts of the Group VIII noble metals in the catalyst bed are controlled either by the relative amounts of the Group VIII noble metal-containing components employed in their respective groups of active carbon carrier particles or by the relative amounts of active carbon carrier particles employed in their respective groups of active carbon carrier particles. In this embodiment, when each of the first and second groups of active carbon carrier particles are uniformly distributed throughout the catalyst bed, the Group VIII noble metal-containing components are also uniformly distributed throughout the catalyst bed. Alternatively in this embodiment, the catalyst bed is layered and has (1) at least one layer comprising substantially only the aforesaid first group of particles and (2) at least one layer comprising substantially only the aforesaid second group of particles, and thus the Group VIII noble metal-containing components are not uniformly distributed throughout the catalyst bed.

In this later case of a layered bed, the aqueous isophthalic acid solution is passed first through a first layer comprising substantially only the aforesaid first group of particles containing only a first Group VIII noble metal-containing component and then through a second layer comprising substantially only the aforesaid second group of particles containing only the second Group VIII noble metal-containing component. Typically the weight ratio of the first layer to the second layer is in the range of from about 1:100, preferably from about 1:20, to about 1:2, preferably to about 1:4. Similarly the residence time of the aqueous isophthalic acid solution in the first layer is from about 1:2 to about 1:100 of the total residence time of the solution in the catalyst bed. Thereafter the aqueous solution is withdrawn from the catalyst bed directly or after passing the aqueous solution through a third layer comprising, for example, substantially only either the aforesaid first group of particles containing only the first Group VIII noble metal-containing component or a third group of particles comprising a third Group VIII noble metal-containing component.

The present invention will be more clearly understood from the following specific examples.

EXAMPLES 1–3

In each of Examples 1–3, a pilot plant reactor of the down-flow type and equipped with a fixed catalyst bed one inch in diameter and 6.5 inches in length was used. The catalyst bed was constituted in Example 1 by a particulate commercial palladium-on-carbon catalyst (40 grams; 0.5 weight percent Pd; Engelhard) alone and in Examples 2 and 3 by a particulate layer of rhodium-on-carbon catalyst (4 grams; 0.5 weight percent Rh) and a particulate layer of the same commercial palladium-on-carbon catalyst (36 grams). In Example 2, the palladium-on-carbon catalyst was the upper layer, and in Example 3, the rhodium-on-carbon catalyst was the upper layer.

The rhodium-on-carbon catalyst was prepared from rhodium nitrate as a precursor, at a pH value of 2 in water, and using North American active carbon G-201 as support by the procedure of U.S. Pat. No. 4,728,630. All catalysts were hot washed and aged for 72 hours in an autoclave in the presence of terephthalic acid and hydrogen. The reactor was operated at a temperature of about 221° C. (430° F.) and at hydrogen partial pressures of about 40 psi. The total reactor pressure was about 380 psig, respectively. Crude isophthalic acid slurry containing about 20 weight percent of isophthalic acid was fed to the reactor at a feed rate of 1.8 kg of solution per hour. The b*-value, fluorescence index and optical densities at 340 and 400 nm of the resulting purified isophthalic acid were measured and are reported in Table 1 below.

TABLE I

|  | Example 1 | Example 2 | Example 3 |
|---|---|---|---|
| b*-value | 1.28 | 1.08 | 0.87 |
| Fluorescence index | 0.39 | 0.37 | 0.36 |
| Optical density at 340 nm | 0.81 | 0.62 | 0.56 |
| Optical density at 400 nm | 0.096 | 0.066 | 0.033 |

From the above description, it is apparent that, while only certain embodiments have been set forth, alternative embodiments and various modifications will be apparent from the above description to those skilled in the art. These alternatives are considered equivalents and are within the spirit and scope of the present invention.

Having described the invention, what is claimed is:

1. A method for the purification of crude isophthalic acid, comprising:

passing a solution of said crude isophthalic acid in a polar solvent at a temperature of from about 100° C. to about 300° C. and at a pressure that is sufficient to maintain the solution substantially in the liquid phase, through a particulate catalyst bed and in the presence of hydrogen; said particulate catalyst bed comprising, Group VIII noble metal-containing components comprising at least two of palladium-, platinum-, rhodium-, ruthenium-, osmium- and iridium-containing components, supported on active carbon carrier particles; and thereafter cooling the resulting hydrogenated solution to effect separation of the resulting purified isophthalic acid from said solution by crystallization.

2. The method of claim 1 wherein the Group VIII noble metal-containing components are supported on the same active carbon carrier particles and there is a substantially uniform distribution of each of the Group VIII noble metal-containing components throughout the catalyst bed.

3. The method of claim 1 wherein one of the Group VIII noble metal-containing components is supported on a first group of the active carbon carrier particles and a second Group VIII noble metal-containing component is supported on a second group of the active carbon carrier particles, and the aforesaid first group of particles is separate and distinct from the aforesaid second group of particles.

4. The method of claim 3 wherein each of the first and second groups of particles is substantially uniformly distributed throughout the catalyst bed.

5. The method of claim 3 wherein the catalyst bed is layered and has at least one layer comprising substantially only the aforesaid first group of particles and at least one layer comprising substantially only the aforesaid second group of particles.

6. The method of claim 5 wherein the solution is passed first through a first layer comprising substantially only the aforesaid first group of particles and then through a second layer comprising substantially only the aforesaid second group of particles.

7. The method of claim 6 wherein after being passed through the second layer and before being withdrawn from the catalyst bed, the solution is passed through a third layer comprising substantially only either the aforesaid first group of particles or a third group of particles comprising a third Group VIII noble metal-containing component.

8. The method of claim 1 wherein the isophthalic solution is maintained at a temperature of about 200° C. to about 250° C., and wherein hydrogen is present in an amount about twice the amount stoichiometrically required to hydrogenate all hydrogenatable impurities.

9. The method of claim 1 wherein the space velocity of the isophthalic acid solution through the catalyst bed is about 5 hours$^{-1}$ to about 25 hours$^1$.

10. The method of claim 9 wherein the space velocity of the aqueous isophthalic acid sol the catalyst bed is about 10 hours$^{-1}$ to about 25 hours$^3$.

11. The method of claim 6 wherein the residence time of the isophthalic acid solution in said first layer is from about 1:100 about 1:2 of the total residence time of the aqueous isophthalic acid solution in the particulate catalyst bed.

12. The method of claim 1 wherein said Group VIII noble metals are at least two of palladium, rhodium, platinium, ruthenium, osmium, or iridium.

13. The method of claim 12 wherein said Group VIII noble metals comprise palladium and rhodium.

14. The method of claim 1 wherein each Group VIII noble metal is present in the catalyst bed at a same or different concentration in the range of from about 0.01 to about 2 percent by weight, based on the weight of the catalyst bed and calculated as the elemental metal.

15. The method of claim 1 wherein two Group VIII noble metals are present in the catalyst bed at an atomic ratio in the range of from about 1:100 to about 1:1, calculated as the elemental metals.

16. The method of claim 15 wherein the aforesaid two Group VIII noble metals are present in the catalyst bed at an atomic ratio in the range of from about 1:20 to about 1:4, calculated as the elemental metals.

17. The method of claim 6 wherein the first group of particles comprises a rhodium-containing component and the second group of particles comprises a palladium-containing component.

18. The method of claim 6 wherein the first group of particles comprises a palladium-containing component and the second group of particles comprises a rhodium-containing component.

19. The method of claim 1 wherein water is the polar solvent.

* * * * *

UNITED STATES PATENT AND TRADEMARK OFFICE
CERTIFICATE OF CORRECTION

PATENT NO. : 4,933,492

DATED : June 12, 1990

INVENTOR(S) : Hobe Schroeder & Ricky L. Wittman

It is certified that error appears in the above-identified patent and that said Letters Patent is hereby corrected as shown below:

Col. 9, line 8, "25 hours$^1$" should read --25 hours$^{-1}$--;

line 10, "sol" should read --solution through--; and line 11, "25 hours$^3$" should read --25 hours$^{-1}$--.

Signed and Sealed this

Third Day of September, 1991

*Attest:*

HARRY F. MANBECK, JR.

*Attesting Officer*     *Commissioner of Patents and Trademarks*